United States Patent
Nowak et al.

(10) Patent No.: US 10,792,586 B2
(45) Date of Patent: *Oct. 6, 2020

(54) FOLDED FRACTIONATION COLUMN AND PROCESS

(71) Applicant: UOP LLC, Des Plaines, IL (US)

(72) Inventors: Brian J. Nowak, Orchard Park, NY (US); Kevin J. Richardson, Hamburg, NY (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/100,071

(22) Filed: Aug. 9, 2018

(65) Prior Publication Data

US 2019/0299121 A1  Oct. 3, 2019

Related U.S. Application Data

(63) Continuation-in-part of application No. 15/940,776, filed on Mar. 29, 2018.

(51) Int. Cl.
| | |
|---|---|
| *B01D 1/14* | (2006.01) |
| *B01D 3/32* | (2006.01) |
| *B01D 3/40* | (2006.01) |
| *C07C 7/04* | (2006.01) |
| *B01D 3/14* | (2006.01) |

(52) U.S. Cl.
CPC ............ *B01D 3/324* (2013.01); *B01D 3/141* (2013.01); *B01D 3/40* (2013.01); *C07C 7/04* (2013.01); *B01D 1/14* (2013.01)

(58) Field of Classification Search
CPC .......... B01D 3/14; B01D 3/141; B01D 3/143; B01D 3/42; B01D 3/4205; B01D 3/4211; B01D 3/4216; B01D 3/4222; B01D 3/4227; B01D 3/4233; B01D 3/4238; B01D 3/4244; B01D 3/425; B01D 3/4255; B01D 3/4261; B01D 3/4266; B01D 3/4272;
(Continued)

(56) References Cited

U.S. PATENT DOCUMENTS

| | | | |
|---|---|---|---|
| 4,096,574 A | 6/1978 | Christie | |
| 4,234,391 A * | 11/1980 | Seader | ............... B01D 3/141 |
| | | | 165/104.26 |

(Continued)

FOREIGN PATENT DOCUMENTS

| | | |
|---|---|---|
| TW | 201731813 A | 9/2017 |
| WO | 2014130066 A1 | 8/2014 |

OTHER PUBLICATIONS

R.M. Price, lecture notes titled "Distillation I: Principles", 2003, available online at: http://facstaff.cbu.edu/rprice/lectures/distill.html (Year: 2003).*

(Continued)

*Primary Examiner* — Jonathan Luke Pilcher

(57) ABSTRACT

An apparatus and process doubles the number of trays in a single fractionation column. A dividing wall is used to isolate a first side from a second side and fractionation on trays on each side is independent of the other. A transition vapor stream is ducted from a top of a first side to the bottom of the second side, and a transition liquid stream is ducted from a bottom of the second side to the top of the first side.

10 Claims, 2 Drawing Sheets

(58) Field of Classification Search
CPC .. B01D 3/4277; B01D 3/4283; B01D 3/4288; B01D 3/4294
USPC .......................................... 202/154; 203/75
See application file for complete search history.

(56) References Cited

U.S. PATENT DOCUMENTS

| | | | |
|---|---|---|---|
| 4,894,145 A * | 1/1990 | Jensen | B01D 3/4244 202/160 |
| 6,348,637 B1 | 2/2002 | Harris | |
| 6,483,002 B1 | 11/2002 | O'Brien | |
| 7,091,252 B2 | 8/2006 | Smith, et al. | |
| 7,528,290 B2 * | 5/2009 | Zimmermann | B01D 1/007 202/152 |
| 8,877,014 B2 | 11/2014 | Corradi et al. | |
| 9,550,133 B2 * | 1/2017 | Favilli | B01D 1/28 |
| 9,908,060 B2 * | 3/2018 | Wakabayashi | B01D 1/28 |
| 2009/0114524 A1 | 5/2009 | Sechrist | |
| 2013/0256115 A1 * | 10/2013 | Wakabayashi | B01D 1/28 202/154 |
| 2014/0158521 A1 | 6/2014 | Ablin et al. | |
| 2019/0282920 A1 | 9/2019 | Schon et al. | |

OTHER PUBLICATIONS

Mane et.al., A New Intensified Heat Integration in Distillation Column, Department of Chemical Engineering, Indian Institute of Technology—Kharagpur, West Bengal 721 302, India, Ind. Eng. Chem. Res., 2010, 49 (19), pp. 9534-9541.

International Search Report from corresponding PCT application No. PCT/US2019/024491, dated Jun. 13, 2019.

Written Opinion from corresponding PCT application No. PCT/US2019/024491, dated Jun. 6, 2019.

* cited by examiner

FOLDED FRACTIONATION COLUMN AND PROCESS

CROSS-REFERENCE TO RELATED APPLICATION

This application is a Continuation-In-Part of copending application Ser. No. 15/940,776 filed Mar. 29, 2018, the contents of which cited application are hereby incorporated by reference in its entirety.

FIELD

The field relates to distillation in a fractionation column.

BACKGROUND

The recovery and purification of a desired compound from another compound in a mixture may be accomplished by a sequence of distillation operations. The sequence may consist of distillation columns to separate both lower and higher boiling components from the desired compounds and generally includes a distillation operation to separate a mixed stream of the desired compound from another compound closest to it in boiling point. Separating a desired olefin from its alkane to provide an olefin product or "polymer grade" olefin, which can be used for polymer manufacturing in a downstream operation can require many distillation stages. For example, the ethylene/ethane and propane/propylene separations by distillation are both energy and capital intensive due to the relative volatility of species to be separated, feed composition, and product purity requirements of "polymer grade" propylene.

Capital intensity is high because numerous trays are necessary to make the fine and difficult separation that polymer grade olefins require. Distillation columns of 150 trays are typical for a propylene/propane splitter column resulting in very tall columns. Ways are sought to reduce the height of these fractionation columns.

SUMMARY

An apparatus and process doubles the number of trays in a single fractionation column. A dividing wall is used to isolate a first side from a second side and fractionation on trays on each side is independent of the other. A transition vapor stream is ducted from a top of a first side to the bottom of the second side, and a transition liquid stream is ducted from a bottom of the second side to the top of the first side. Data may be received from a stream in fluid communication with the foregoing process and apparatus. The data may be transmitted, analyzed and used as basis for adjusting conditions in the process.

DETAILED DESCRIPTION

Figure 1:
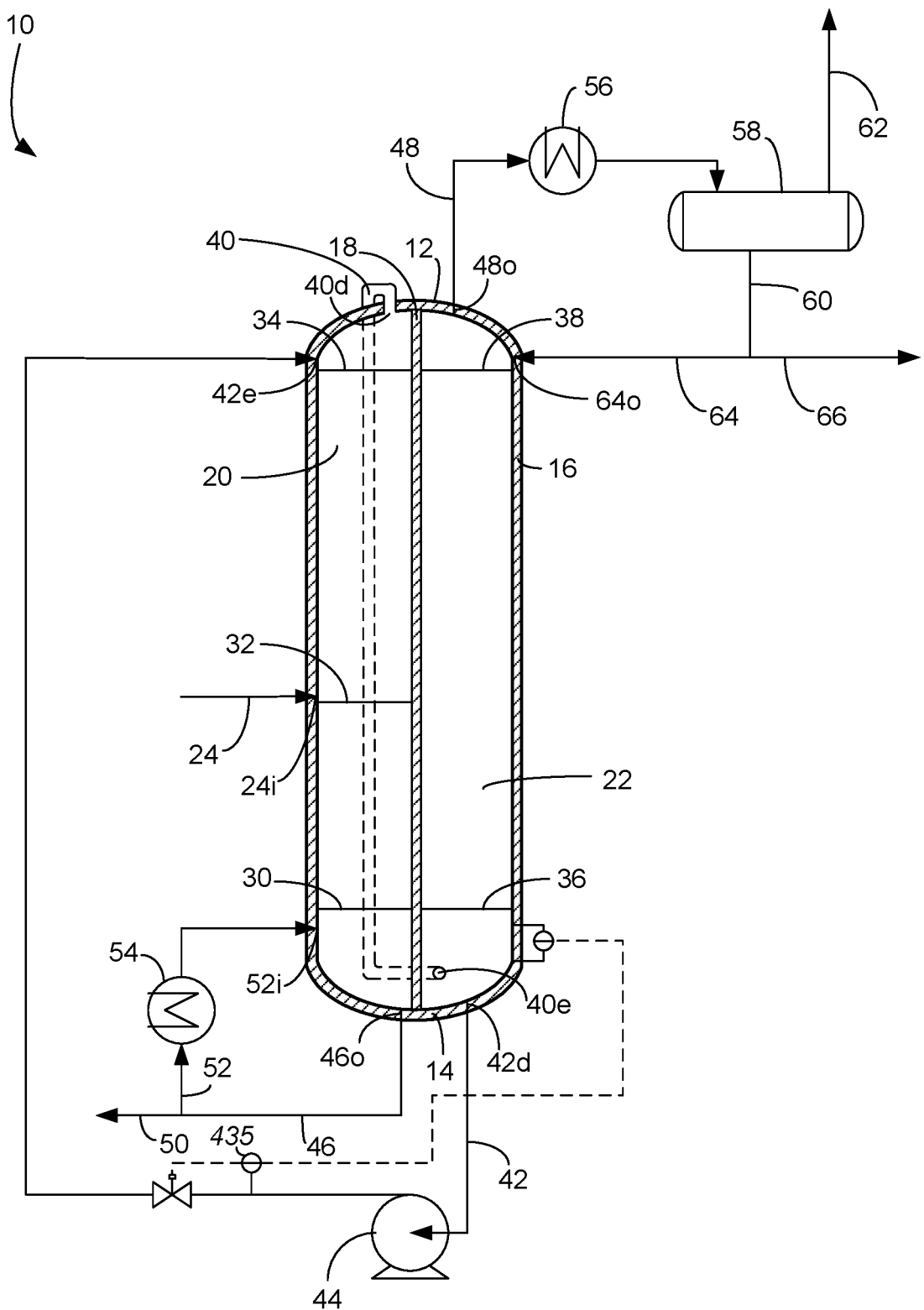
FIG. 1 is a simplified schematic diagram of a fractionation column.

FIG. 1 schematically illustrates a fractionation column applicable to the separation of any two materials of different boiling points and are particularly useful for materials with a difference in boiling points of about 11° C. (~20° F.) or less. Non-limiting examples of separations suitable for the fractionation column 10 include: paraffin/olefin separations including ethane/ethylene, propane/propylene, butane/butylene, pentane/pentene; isomer/normal separations of these compounds (e.g., isobutane/butane); straight chain/branched or multi-chain paraffin separations; ethyl benzene/styrene; mixed xylenes separations (e.g., para/ortho/meta); and others.

Those skilled in the art and guided by the teachings herein provided will recognize and appreciate that the illustrated fractionation column 10 has been simplified by the elimination of various usual or customary pieces of process equipment including some heat exchangers, control systems, pumps, and the like. It may also be discerned that the process flows depicted in FIG. 1 may be modified in many aspects without departing from the scope of this disclosure. The fractionation column 10 comprises a top 12, a bottom 14 and a sidewall 16 extending between the top and bottom. The sidewall 16 may define a tube and is preferably cylindrical with a hollow interior. The side wall 16 is typically solid steel and may have an outer insulative layer. The top 12 and the bottom 14 may be hemi-spherical and be contiguous with the top and bottom of the sidewall 16, respectively. A dividing wall 18 extends longitudinally between the top 12 and the bottom 14 and laterally between sides of the sidewall 16, so as to divide a first side 20 of the column 10 from a second side 22 of the column. Suitably, the dividing wall 18 extends longitudinally completely between the top 12 and the bottom 14 and laterally completely between the first side 20 and the second side 22 of the column 10, so as to prevent material from traveling from the first side 20 to the second side 22 except through a duct or intentional opening. The first side 20 does not communicate with the second side 22 through the wall 18 except through a duct or intentional opening. As such, the first side 20 is isolated from the second side 22 by the dividing wall 18.

A feed stream comprising a first material having a lower boiling point and a second material having a higher boiling point than the first material to be separated by fractionation is introduced into the column 10 in a feed line 24 through a feed inlet 24$i$ in the side wall. The feed line 24 may feed the first side 20 through the feed inlet 24$i$ as shown in FIG. 1. However, the feed line 24 may feed the feed stream to the second side 22. The fractionation column 10 receives the feed stream in line 24 and fractionates the first material from the second material in the feed stream by boiling the more volatile first material from the less volatile second material.

The column 10 contains numerous trays but only five trays are illustrated: the bottom tray 30, the feed tray 32, the first top tray 34, the second bottom tray 36 and the top tray 38. Numerous trays are provided between the first top tray 34 and the bottom tray 30 and between the second bottom tray 36 and the top tray 38 but are not shown. No trays are provided above the first top tray 34 or the top tray 38 or below the second bottom tray 36 and the bottom tray 30. The top 12 of the column 10 is above the first top tray 34 and the top tray 38. The bottom 14 of the column 10 is below the bottom tray 30 and the second bottom tray 36.

In the fractionation column 10 the feed stream is distilled causing more volatile materials to ascend in the column from tray to tray and less volatile materials to descend in the column from tray to tray on both sides 20, 22 of the column.

A vapor discharge 40$d$ is provided at the top 12 of the column 10, preferably in the top 12 of the column, in the first side 20 to emit vapor from the top 12 in the first side. The vapor discharge 40$d$ may be the only way vapor may exit the first side 20 or the top 12 of the first side of the column 10. The vapor discharge 40$d$ is preferably above the first top tray 34 in the first side 20. The vapor discharge 40d feeds a vapor duct having a first end at the vapor discharge and a second end of the duct at a vapor entry 40e at the bottom 14 of the column 10 in the second side 22. The duct 40 may extend through the column 10 such as through the dividing wall 18. It is also envisioned that the dividing wall is double walled defining the vapor duct 40 between the two walls with the vapor discharge 40d comprising an opening in the wall on the first side 20 at the top 12 and the vapor entry 40e comprising an opening in the wall on the second side 22 at the bottom 14 (not shown). The vapor entry 40e is preferably below the second bottom tray 36 in the second side 22. Preferably, the vapor duct 40 extends outside of the column 10, as shown in phantom, and the vapor discharge 40d and the vapor entry 40e are fashioned in the sidewall 16 or the top 12 or bottom 14 of the column, respectively. A transition vapor stream is passed in the duct 40 from the top 12 in the first side 20 of the column 10 to the bottom 14 in the second side 22 of the column to be further rectified in the second side.

The column 10 comprises a liquid discharge 42d at the bottom 14, preferably in the bottom, of the column in the second side 22. The liquid discharge 42d is preferably below the second bottom tray 36 in the second side 22. A liquid duct 42 has a first end at the liquid discharge 42d, and the liquid duct has a second end at a liquid entry 42e at or in the top 12 of the column 10 in the first side 20. The liquid entry 42e is preferably above the first top tray 34 in the first side 20. The liquid duct 42 may include a pump 44 for pumping the liquid up the liquid duct from the bottom 14 to the top 12 of the column 10. The liquid duct 42 extends from the suction side to the discharge side of the pump 44. The liquid duct 42 passes a transition liquid stream from the bottom 14 of the second side 22 of the column 10 to the top 12 of the first side 20 of the column to be further stripped in the first side.

The fractionation column 10 has a bottoms outlet 46o at the bottom 14, preferably in the bottom, of the column in the first side 20 and an overhead outlet 48o at the top 12, preferably in the top, of the column in the second side 22. The bottoms outlet 46o is preferably below the bottom tray 30 in the first side 20. A bottoms line 46 withdraws a bottoms liquid stream from the bottom 14 of the first side 20 of the column 10 through the bottoms outlet 46o. A bottoms product line 50 may take a portion of the bottoms liquid stream from the bottoms line 46 as bottoms product. The bottoms outlet 46o in the bottom 14 of the column 10 in the first side 20 may be in upstream communication with the bottoms product line 50. The bottoms product line 50 transports a bottoms product stream of the second material.

A reboil line 52 may take a reboil portion of the bottoms liquid stream in the bottoms line 46 to a reboil heater 54 to reboil the bottoms liquid and return the reboiled vapor to the column 10, perhaps to the bottom of the column through a reboil inlet 52i at, and preferably in, the bottom of the column in the first side 20. The reboil inlet 52i is preferably below the bottom tray 30 in the first side 20. The reboil heater 54 may be in downstream communication with the bottoms outlet 46o in the column 10, and a reboil inlet 52i in the first side 20 of the column, at or perhaps in the bottom of the column, may be in downstream communication with the reboil heater 54. In an alternative embodiment, no reboiler is used, and the bottoms product line 50 takes all of the bottoms liquid stream from the bottoms outlet as the bottoms product. Heat input to the column may be provided by preheating the feed stream in feed line 24 or by providing a vaporous media stream, such as steam, at or in the bottom 16 of the column 10 in the first side 20 or the second side 22.

An overhead line 48 is in downstream communication with the overhead outlet 48o in the top 12 of the column 10 in the second side 22 for removing an overhead vapor stream from the top 12 in the second side 22 of the column 10. The overhead outlet 48o is preferably above the top tray 38 in the second side 20.

A cooler 56 may be in downstream communication with the overhead outlet 48o to cool and condense at least part of the overhead vapor stream in the overhead line 48. A receiver 58 comprising a separator vessel may be in downstream communication with the overhead outlet 48o, the overhead line 48 and the cooler 56 for receiving the condensed vapor stream from the cooler 56. The condensed vapor stream separates in the receiver into a net vapor stream and a condensate stream. A net overhead vapor line 62 may extend from a top of the receiver 58 for transporting and recovering a net overhead vapor stream. The net overhead vapor line may be in downstream communication with the receiver 58. A condensate line 60 extends from a bottom of the receiver 58 for transporting an overhead condensate stream. A reflux inlet 64o in the top 12 of the column in the second side 22 may be in downstream communication with the overhead outlet 48O. The reflux inlet 64o is preferably above the top tray 38 in the second side 22. A reflux line 64 transports a reflux stream taken from the overhead condensate stream as a reflux portion of the overhead condensate stream in the condensate line 60 to the top 12 in the second side 22 of the column 10. The reflux inlet 64o may be in downstream communication with the reflux line 64. A net overhead liquid line 66 in downstream communication with the receiver 58 transports to recovery a net overhead liquid stream taken from the overhead condensate stream in the condensate line 60 comprising the first material.

In some cases, the receiver 58 may collect an aqueous stream from the condensed vapor stream which is recovered in an aqueous line perhaps coming off of a boot (not shown) from the receiver. Additionally, the net overhead vapor line 62 may be optional if the condenser 56 is operated to completely condense the overhead vapor stream from the overhead outlet 48O.

Operating conditions for a fractionation column are confined by the physical properties of the materials being separated in the column. Operating temperature and pressure of a column may be varied within these confines to minimize the operating cost of the column and accommodate other commercial objectives. The operating temperature may range from very low temperatures used in cryogenic separations to temperatures which challenge the thermal stability of the compounds. Conditions suitable for the subject process therefore include a temperature in the broad range of from about −50° C. to about 400° C. The column is operated at a pressure sufficient to maintain at least a portion of the feed compounds present as a liquid.

Any of the above conduits, unit, devices, vessels, scaffolding, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

A sensor 435 on the liquid duct 42 may communicate data such as to a liquid level control in the bottom 14 of the second side 22 and to a flow control valve on the liquid duct. The sensor may be a flow meter, a temperature sensor or a pressure gauge. The sensor may transmit or communicate data to an offsite location.

As will be appreciated by one of skill in the art upon reading the following disclosure, various aspects described herein may be embodied as a method, a computer system, or a computer program product. Accordingly, those aspects may take the form of an entirely hardware embodiment, an entirely software embodiment or an embodiment combining software and hardware aspects. Furthermore, such aspects may take the form of a computer program product stored by one or more non-transitory computer-readable storage media having computer-readable program code, or instructions, embodied in or on the storage media. Any suitable computer-readable storage media may be utilized, including hard disks, CD-ROMs, optical storage devices, magnetic storage devices, and/or any combination thereof. In addition, various signals representing data or events as described herein may be transferred between a source and a destination in the form of electromagnetic waves traveling through signal-conducting media such as metal wires, optical fibers, and/or wireless transmission media (e.g., air and/or space).

Figure 2:
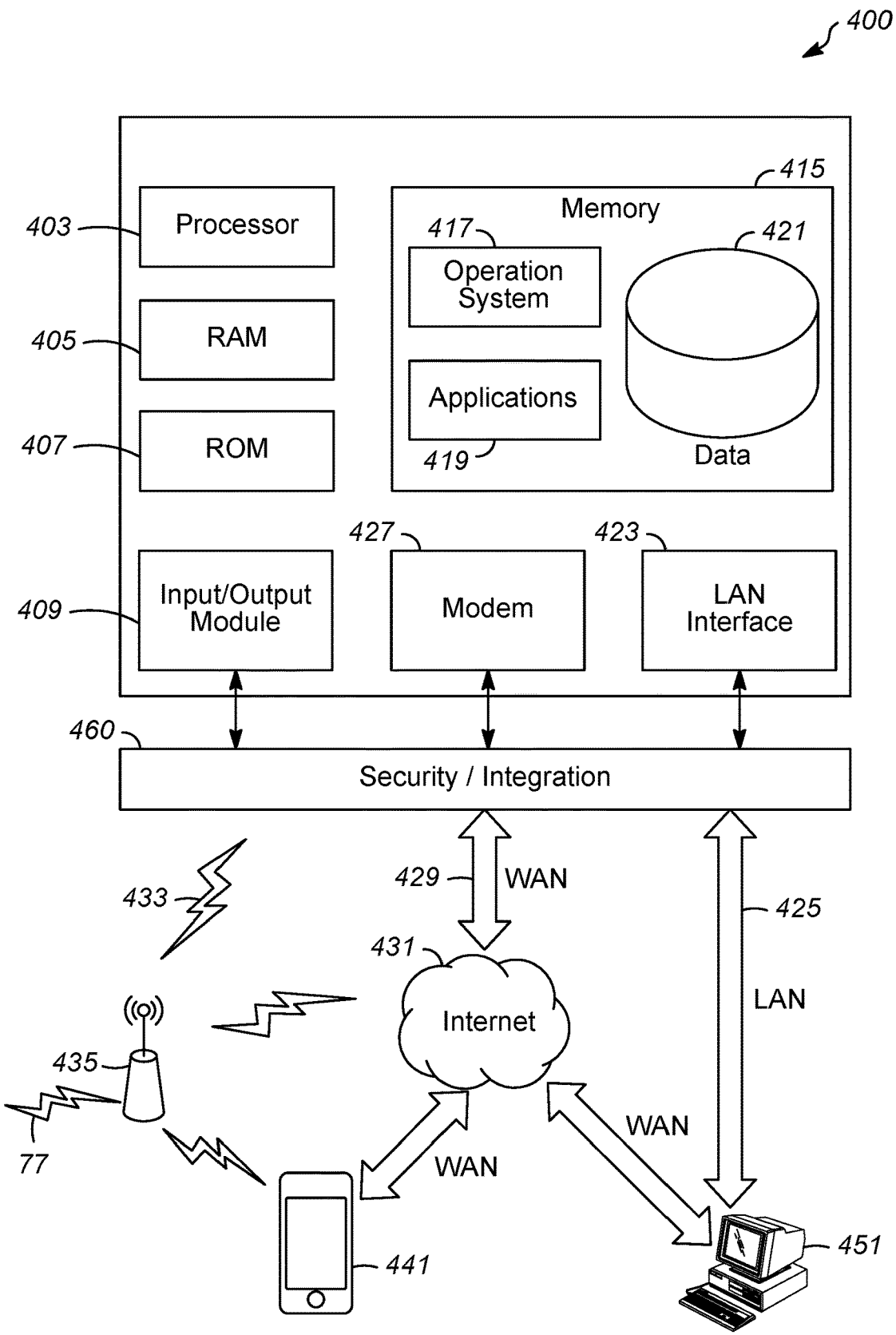
FIG. 2 illustrates a block diagram.

FIG. 2 illustrates a block diagram of a process mode detection system 401 in a sensor data analysis system 400 that may be used with the fractionation column 10 according to one or more illustrative embodiments of the disclosure. The system 401 may be used to collect data from and/or operate or control the fractionation column 10. The system 401 may have a processor 403 for controlling overall operation of the system 401 and its associated components, including RAM 405, ROM 407, input/output module 409, and memory 415. The system 401, along with one or more additional devices (e.g., terminals 441, 451) may correspond to any of multiple systems or devices, such as mobile computing devices (e.g., smartphones, smart terminals, tablets, and the like) and/or vehicular-based computing devices, configured as described herein for collecting and analyzing sensor data from mobile devices associated with vehicles, particularly acceleration data and location data.

Input/output (I/O) 409 may include a microphone, keypad, touch screen, and/or stylus through which a user of the system 401 may provide input, and may also include one or more of a speaker for providing audio output and a video display device for providing textual, audiovisual and/or graphical output. Software may be stored within memory 415 and/or storage to provide instructions to processor 403 for enabling system 401 to perform various functions. For example, memory 415 may store software used by the system 401, such as an operating system 417, application programs 419, and an associated internal database 421. Processor 403 and its associated components may allow the system 401 to execute a series of computer-readable instructions to transmit or receive data, analyze data, and store analyzed data.

The system 401 may operate in a networked environment supporting connections to one or more remote computers, such as terminals/devices 441 and 451. System 401, and related terminals/devices 441 and 451, may include devices or sensors associated with equipment, streams, or materials of the fractionation column 10 or the refinery comprising the fractionation column, including devices on-line or outside of equipment, streams, or materials, that are configured to receive and process data. Thus, the system 401 and terminals/devices 441 and 451 may each include personal computers (e.g., laptop, desktop, or tablet computers), servers (e.g., web servers, database servers), sensors, measurement devices, communication systems, or mobile communication devices (e.g., mobile phones, portable computing devices, and the like), and may include some or all of the elements described above with respect to the system 401.

The network connections depicted in FIG. 2 include a local area network (LAN) 425 and a wide area network (WAN) 429, and a wireless telecommunications network 433, but may also include other networks. When used in a LAN networking environment, the system 401 may be connected to the LAN 425 through a network interface or adapter 423. When used in a WAN networking environment, the system 401 may include a modem 427 or other means for establishing communications over the WAN 429, such as network 431 (e.g., the Internet). When used in a wireless telecommunications network 433, the system 401 may include one or more transceivers, digital signal processors, and additional circuitry and software for communicating with wireless computing devices 441 (e.g., mobile phones, short-range communication systems, telematics devices) via one or more network devices 435 (e.g., base transceiver stations) in the wireless network 433. Network devices 435 can comprise sensors in communication with various streams in lines in the fractionation column 10 or the refinery comprising the fractionation column for determining compositions and/or conditions of the stream therein. The network devices 435 can transmit measurement signals from a transmitter in the network device through either the wireless network 433, the WAN 429 or the LAN 425.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, WiFi, and WiMAX, is presumed, and the various computing devices spent catalyst measurement system components described herein may be configured to communicate using any of these network protocols or technologies.

Also illustrated in FIG. 2 is a security and integration layer 460, through which communications may be sent and managed between the system 401 (e.g., a user's personal mobile device, a refinery-based system, external server, etc.)

and the remote devices (441 and 451) and remote networks (425, 429, and 433). The security and integration layer 460 may comprise one or more separate computing devices, such as web servers, authentication servers, and/or various networking components (e.g., firewalls, routers, gateways, load balancers, etc.), having some or all of the elements described above with respect to system 401. As an example, a security and integration layer 460 of a mobile computing device, refinery-based device, or a server operated by a provider, an institution, governmental entity, or other organization, may comprise a set of web application servers configured to use secure protocols and to insulate the system 401 from external devices 441 and 451. In some cases, the security and integration layer 460 may correspond to a set of dedicated hardware and/or software operating at the same physical location and under the control of same entities as system 401. For example, layer 460 may correspond to one or more dedicated web servers and network hardware in an organizational datacenter or in a cloud infrastructure supporting a cloud-based spent catalyst measurement system. In other examples, the security and integration layer 460 may correspond to separate hardware and software components which may be operated at a separate physical location and/or by a separate entity.

As discussed below, the data transferred to and from various devices in sensor data analysis system 400 may include secure and sensitive data, such as measurement data, flow control data, concentration data, and instructions. In at least some examples, transmission of the data may be performed based on one or more user permissions provided. Therefore, it may be desirable to protect transmissions of such data by using secure network protocols and encryption, and also to protect the integrity of the data when stored in a database or other storage in a mobile device, analysis server, or other computing devices in the sensor data analysis system 400, by using the security and integration layer 460 to authenticate users and restrict access to unknown or unauthorized users. In various implementations, security and integration layer 460 may provide, for example, a file-based integration scheme or a service-based integration scheme for transmitting data between the various devices in the sensor data analysis system 400. Data may be transmitted through the security and integration layer 460, using various network communication protocols. Secure data transmission protocols and/or encryption may be used in file transfers to protect to integrity of the driving data, for example, File Transfer Protocol (FTP), Secure File Transfer Protocol (SFTP), and/or Pretty Good Privacy (PGP) encryption.

In other examples, one or more web services may be implemented within the system 401, in the sensor data analysis system 400 and/or the security and integration layer 460. The web services may be accessed by authorized external devices and users to support input, extraction, and manipulation of the data (e.g., sensing data, concentration data, flow control data, etc.) between the system 401 in the sensor data analysis system 400. Web services built to support the sensor data analysis system 400 may be cross-domain and/or cross-platform, and may be built for enterprise use. Such web services may be developed in accordance with various web service standards, such as the Web Service Interoperability (WS-I) guidelines. In some examples, a flow control data and/or concentration data web service may be implemented in the security and integration layer 460 using the Secure Sockets Layer (SSL) or Transport Layer Security (TLS) protocol to provide secure connections between servers (e.g., the system 401) and various clients 441 and 451 (e.g., mobile devices, data analysis servers, etc.). SSL or TLS may use HTTP or HTTPS to provide authentication and confidentiality.

In other examples, such web services may be implemented using the WS-Security standard, which provides for secure SOAP messages using XML encryption. In still other examples, the security and integration layer 460 may include specialized hardware for providing secure web services. For example, secure network appliances in the security and integration layer 460 may include built-in features such as hardware-accelerated SSL and HTTPS, WS-Security, and firewalls. Such specialized hardware may be installed and configured in the security and integration layer 460 in front of the web servers, so that any external devices may communicate directly with the specialized hardware.

In some aspects, various elements within memory 415 or other components in sensor data analysis system 400, may include one or more caches, for example, CPU caches used by the processing unit 403, page caches used by the operating system 417, disk caches of a hard drive, and/or database caches used to cache content from database 421. For embodiments including a CPU cache, the CPU cache may be used by one or more processors in the processing unit 403 to reduce memory latency and access time. In such examples, a processor 403 may retrieve data from or write data to the CPU cache rather than reading/writing to memory 415, which may improve the speed of these operations. In some examples, a database cache may be created in which certain data from a database 421 (e.g., an operating parameter database, a concentration database, correlation database, etc.) is cached in a separate smaller database on an application server separate from the database server. For instance, in a multi-tiered application, a database cache on an application server can reduce data retrieval and data manipulation time by not needing to communicate over a network with a back-end database server. These types of caches and others may be included in various embodiments, and may provide potential advantages in certain implementations of retrieving data, collecting data, recording stat, processing data, and analyzing data, such as faster response times and less dependence on network conditions when transmitting/receiving data.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as GSM, CDMA, WiFi, and WiMAX, is presumed, and the various computer devices and system components described herein may be configured to communicate using any of these network protocols or technologies.

Additionally, one or more application programs 419 may be used by the system 401 within a sensor data analysis system 400 (e.g., flow control software applications, device configuration software applications, and the like), including computer executable instructions for receiving and storing data from refinery-based systems, and/or mobile computing devices, analyzing the data to determine the composition, flow rates and/or conditions of streams at desired locations; analyzing data to determine the setting or adjustment to the flow of streams in the lines; analyzing data to determine the conditions or adjustment to conditions in vessels; and determining and configuring the mobile computing device based on the retrieved and analyzed data, and/or performing other related functions as described herein.

The processor 403 may be configured to issue or recommend a command message to adjust conditions in the fractionation column 10. The command message may be transmitted from the process mode detection system 401 in an encrypted or unencrypted message that commands one or more adjustments to conditions in the fractionation column 10. The command may be communicated through the I/O module 409, the modem 427 or the LAN interface 423 through the security/integration layer 460 and received by a network device 435 or terminals 441, 451 in the fractionation column 10 or the refinery comprising the fractionation column to cause adjustments or halting/starting of one or more operations in the fractionation column 10 or the refinery. The command message may be transmitted to a terminal 441, 451 for processing and/or execution. In an alternative embodiment, the command may be directly communicated, either wirelessly or in a wired fashion, to physical components in the fractionation column 10 or in the refinery containing the fractionation column such that the physical components include an network device 435 to receive the commands and execute the command. Terminals 441, 451 may automatically signal execution of the command or a prompt to an operator to manually execute the adjustment. Such adjustment command messages can be transmitted back to the fractionation column 10 to be received and executed to modify or improve performance of the fractionation column.

SPECIFIC EMBODIMENTS

While the following is described in conjunction with specific embodiments, it will be understood that this description is intended to illustrate and not limit the scope of the preceding description and the appended claims.

A first embodiment of the invention is a system comprising at least one processor; at least one memory storing computer-executable instructions; and at least one receiver configured to receive data from a sensor on a column for fractionating a first material from a feed stream of the first material and a second material, the column comprising a column comprising a top, a bottom and a sidewall extending therebetween, a dividing wall extending between the top and the bottom and between sides of the sidewall so as to divide a first side of the column from a second side of the column; a feed inlet in the sidewall for introducing the feed stream into the column, a vapor discharge at the top of the column in the first side, a duct having a first end at the vapor discharge, a second end of the duct at a vapor entry at a bottom of the column in the second side; a liquid discharge at the bottom of the column in the second side, a duct having a first end at the liquid discharge, a second end of the duct at a liquid inlet at a top of the column in the first side; a bottoms outlet in the bottom of the column in the first side; and an overhead outlet in the top of the column in the second side. An embodiment of the invention is one, any or all of prior embodiments in this paragraph up through the first embodiment in this paragraph further comprising an input/output device to collect the data. An embodiment of the invention is one, any or all of prior embodiments in this paragraph up through the first embodiment in this paragraph wherein the processor may be configured to evaluate the data. An embodiment of the invention is one, any or all of prior embodiments in this paragraph up through the first embodiment in this paragraph wherein the processor may be configured to correlate the data. An embodiment of the invention is one, any or all of prior embodiments in this paragraph up through the first embodiment in this paragraph further comprising a transmitter to transmit a signal to the system. An embodiment of the invention is one, any or all of prior embodiments in this paragraph up through the first embodiment in this paragraph wherein the signal may comprise instructions. An embodiment of the invention is one, any or all of prior embodiments in this paragraph up through the first embodiment in this paragraph wherein the signal may be transmitted to the system. An embodiment of the invention is one, any or all of prior embodiments in this paragraph up through the first embodiment in this paragraph further comprising receiving data from multiple systems wherein one system is the fractionation system. An embodiment of the invention is one, any or all of prior embodiments in this paragraph up through the first embodiment in this paragraph wherein the processor may be further configured to generate quantitative information, predictive information, liquid flow rate, or both. An embodiment of the invention is one, any or all of prior embodiments in this paragraph up through the first embodiment in this paragraph wherein the column may comprise a sensor. An embodiment of the invention is one, any or all of prior embodiments in this paragraph up through the first embodiment in this paragraph wherein at least one receiver may be further configured to receive data of flow rate, temperature or pressure.

A second embodiment of the invention is a method for collecting data from a fractionation column, the method comprising receiving data from a sensor on the fractionation column for fractionating a first material from a feed stream of the first material and a second material, the column comprising a column comprising a top, a bottom and a sidewall extending therebetween, a dividing wall extending between the top and the bottom and between sides of the sidewall so as to divide a first side of the column from a second side of the column; a feed inlet in the sidewall for introducing the feed stream into the column, a vapor discharge at the top of the column in the first side, a duct having a first end at the vapor discharge, a second end of the duct at a vapor entry at a bottom of the column in the second side; a liquid discharge at the bottom of the column in the second side, a duct having a first end at the liquid discharge, a second end of the duct at a liquid inlet at a top of the column in the first side; a bottoms outlet in the bottom of the column in the first side; and an overhead outlet in the top of the column in the second side. An embodiment of the invention is one, any or all of prior embodiments in this paragraph up through the second embodiment in this paragraph further comprising at least one of displaying, or transmitting, or analyzing the received data. An embodiment of the invention is one, any or all of prior embodiments in this paragraph up through the second embodiment in this paragraph further comprising analyzing the received data to generate at least one instruction and transmitting the at least one instruction. An embodiment of the invention is one, any or all of prior embodiments in this paragraph up through the second embodiment in this paragraph further comprising analyzing the received data and generating predictive information. An embodiment of the invention is one, any or all of prior embodiments in this paragraph up through the second embodiment in this paragraph wherein the predictive information may comprise fractionation performance, flow rate data, temperature data or pressure data.

A third embodiment of the invention is a system comprising (a) at least one processor; (b) at least one memory storing computer-executable instructions; and (c) at least one receiver configured to receive data from at least one line in fluid communication with a column for fractionating a first material from a feed stream of the first material and a second material, the column comprising a column comprising a top, a bottom and a sidewall extending therebetween, a dividing wall extending between the top and the bottom and between sides of the sidewall so as to divide a first side of the column from a second side of the column; a feed inlet in the sidewall for introducing the feed stream into the column, a vapor discharge at the top of the column in the first side, a duct having a first end at the vapor discharge, a second end of the duct at a vapor entry at a bottom of the column in the second side; a liquid discharge at the bottom of the column in the second side, a duct having a first end at the liquid discharge, a second end of the duct at a liquid inlet at a top of the column in the first side; a bottoms outlet in the bottom of the column in the first side; and an overhead outlet in the top of the column in the second side. An embodiment of the invention is one, any or all of prior embodiments in this paragraph up through the third embodiment in this paragraph wherein the at least one receiver is further configured to receive data from a sensor on a line in fluid communication with the column. An embodiment of the invention is one, any or all of prior embodiments in this paragraph up through the third embodiment in this paragraph wherein the at least one receiver is further configured to record data on the composition and/or condition of a stream in the at least one line in fluid communication with the column. An embodiment of the invention is one, any or all of prior embodiments in this paragraph up through the third embodiment in this paragraph further comprising an input/output device to collect the data.

A fourth embodiment of the invention is an apparatus for fractionating a first material from a feed stream of the first material and a second material, the column comprising a column comprising a top, a bottom and a sidewall extending therebetween, a dividing wall extending between the top and the bottom and between sides of the sidewall so as to divide a first side of the column from a second side of the column; a feed inlet in the sidewall for introducing the feed stream into the column, a vapor discharge at the top of the column in the first side, a duct having a first end at the vapor discharge, a second end of the duct at a vapor entry at a bottom of the column in the second side; a liquid discharge at the bottom of the column in the second side, a duct having a first end at the liquid discharge, a second end of the duct at a liquid inlet at a top of the column in the first side; an bottoms outlet in the bottom of the column in the first side; and an overhead outlet in the top of the column in the second side. An embodiment of the invention is one, any or all of prior embodiments in this paragraph up through the fourth embodiment in this paragraph wherein the dividing wall extends all the way from the top to the bottom, so the first side does not communicate with the second side through the wall. An embodiment of the invention is one, any or all of prior embodiments in this paragraph up through the fourth embodiment in this paragraph wherein the bottoms outlet in the bottom of the column in the first side is in communication with a bottoms product outlet line. An embodiment of the invention is one, any or all of prior embodiments in this paragraph up through the fourth embodiment in this paragraph further comprising a reboiler heater in communication with the bottoms outlet in the bottom of the column and a reboil inlet in the bottom of the column on the first side in communication with the reboiler heater. An embodiment of the invention is one, any or all of prior embodiments in this paragraph up through the fourth embodiment in this paragraph wherein the overhead outlet in the top of the column in the second side is in communication with an overhead outlet line. An embodiment of the invention is one, any or all of prior embodiments in this paragraph up through the fourth embodiment in this paragraph further comprising a cooler in communication with the overhead outlet. An embodiment of the invention is one, any or all of prior embodiments in this paragraph up through the fourth embodiment in this paragraph further comprising a receiver in communication with the overhead outlet. An embodiment of the invention is one, any or all of prior embodiments in this paragraph up through the fourth embodiment in this paragraph further comprising a reflux inlet in the top of the column in the second side in communication with the overhead outlet. An embodiment of the invention is one, any or all of prior embodiments in this paragraph up through the fourth embodiment in this paragraph further comprising a net overhead liquid line in communication with the receiver. An embodiment of the invention is one, any or all of prior embodiments in this paragraph up through the fourth embodiment in this paragraph further comprising a net overhead vapor outlet line in communication with the receiver. An embodiment of the invention is one, any or all of prior embodiments in this paragraph up through the fourth embodiment in this paragraph further comprising pump in communication with the liquid discharge and the liquid inlet is in communication with the pump.

A fifth embodiment of the invention is a process comprising feeding the feed stream to a fractionation column; passing a transition vapor stream from a top of the first side of the column to a bottom of a second side of the column; passing a transition liquid stream from the bottom of the second side of the column to a top of the first side of the column; withdrawing an overhead vapor stream from a top of the second side of the column; and withdrawing a liquid stream from the bottom of the first side of the column. An embodiment of the invention is one, any or all of prior embodiments in this paragraph up through the fifth embodiment in this paragraph wherein the first side is isolated from the second side by a dividing wall. An embodiment of the invention is one, any or all of prior embodiments in this paragraph up through the fifth embodiment in this paragraph further comprising cooling the overhead vapor stream and separating a net vapor stream from a condensate stream. An embodiment of the invention is one, any or all of prior embodiments in this paragraph up through the fifth embodiment in this paragraph further comprising refluxing a reflux portion from the condensate stream to the top of the column and recovering a net liquid stream. An embodiment of the invention is one, any or all of prior embodiments in this paragraph up through the fifth embodiment in this paragraph further comprising reboiling a reboil portion of the liquid stream and returning the reboil portion to the bottom of the column. An embodiment of the invention is one, any or all of prior embodiments in this paragraph up through the fifth embodiment in this paragraph, further comprising sensing at least one parameter of the process and generating a signal or data from the sensing; and generating and transmitting a signal or data.

A sixth embodiment of the invention is an apparatus for fractionating a first material from a feed stream of the first material and a second material, the column comprising a column comprising a top, a bottom and a sidewall extending therebetween, a dividing wall extending all the way from the top to the bottom and between sides of the sidewall so as to divide a first side of the column from a second side of the column, so the first side does not communicate with the second side through the wall; a feed inlet in the sidewall for introducing the feed stream into the column, a vapor discharge at the top of the column in the first side, a duct having a first end at the vapor discharge, a second end of the duct at a vapor entry at a bottom of the column in the second side; a liquid discharge at the bottom of the column in the second side, a duct having a first end at the liquid discharge, a second end of the duct at a liquid inlet at a top of the column in the first side; an bottoms outlet in the bottom of the column on the first side; and an overhead outlet in the top of the column on the second side. An embodiment of the invention is one, any or all of prior embodiments in this paragraph up through the sixth embodiment in this paragraph further comprising a cooler in communication with the overhead outlet, a receiver in communication with the cooler, and a net overhead liquid outlet line in communication with the receiver. An embodiment of the invention is one, any or all of prior embodiments in this paragraph up through the sixth embodiment in this paragraph wherein the bottoms outlet in the bottom of the column in the first side is in communication with a bottoms product outlet line.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A fractionation system comprising:
   a column for fractionating a first material from a feed stream of said first material and a second material;
   at least one processor;
   at least one non-transitory computer-readable media storing computer-executable instructions; and
   at least one receiver configured to receive data from a sensor on the column for fractionating,
   wherein the column comprises:
      a top, a bottom, and a sidewall extending therebetween,
      a dividing wall extending between the top and the bottom and between sides of the sidewall so as to divide a first side of the column from a second side of the column, each side of the column comprising a plurality of trays, wherein the first side comprises a first top tray and a first bottom tray, and the second side comprises a height between a second top tray and a second bottom tray,
      a feed inlet in the sidewall for introducing the feed stream into the column on the first side at a feed inlet tray, wherein the feed inlet tray is between the first top tray and the first bottom tray, such that the first side comprises a first rectifying section disposed above the feed inlet and a stripping section disposed below the feed inlet,
      a vapor discharge at the top of the column in the first side,
      a vapor duct having a first end at the vapor discharge and a second end at a vapor entry at a bottom of the column in the second side, such that an entirety of the height of the second side comprises a second rectifying section, and wherein the second rectifying section is configured to operate at a lower temperature and pressure than the first rectifying section,
      a liquid discharge at the bottom of the column in the second side,
      a liquid duct having a first end at the liquid discharge and a second end at a liquid inlet at a top of the column in the first side and above the feed inlet in the sidewall,
      a bottoms outlet in the bottom of the column in the first side, wherein a reboiler heater is in fluid communication with the bottoms outlet in the bottom of the column, and
      an overhead outlet in the top of the column in the second side, wherein a cooler is in fluid communication with the overhead outlet.

2. The fractionation system of claim 1 further comprising an input/output device to provide input/output data to the at least one processor.

3. The fractionation system of claim 1 further comprising a transmitter to transmit a signal to the fractionation system.

4. The fractionation system of claim 3 wherein said signal comprises instructions.

5. The fractionation system of claim 1 further comprising at least one receiver configured to receive data from multiple systems wherein one system is the fractionation system.

6. The fractionation system of claim 1 wherein the at least one receiver is configured to receive data of flow rate, temperature, or pressure.

7. A system comprising:
   (a) a column for fractionating a first material from a feed stream of said first material and a second material, the column comprising:
      a top, a bottom and a sidewall extending therebetween,
      a dividing wall extending between the top and the bottom and between sides of the sidewall so as to divide a first side of the column from a second side of the column, each side of the column comprising a plurality of trays, wherein the first side comprises a first top tray and a first bottom tray, and the second side comprises a height between a second top tray and a second bottom tray,
      a feed inlet in the sidewall for introducing the feed stream into the column on the first side at a feed inlet tray, wherein the feed inlet tray is between the first top tray and the first bottom tray, such that the first side comprises a first rectifying section disposed above the feed inlet and a stripping section disposed below the feed inlet,
      a vapor discharge at the top of the column in the first side,
      an uninterrupted vapor duct having a first end at the vapor discharge and a second end at a vapor entry at a bottom of the column in the second side, such that an entirety of the height of the second side comprises a second rectifying section, and wherein the first side of the column is not in fluid communication with the second side of the column through the dividing wall except by said uninterrupted vapor duct which extends a distance greater than the height of the second side, through the column, and through the dividing wall,
      a liquid discharge at the bottom of the column in the second side,
      a liquid duct having a first end at the liquid discharge and a second end at a liquid inlet at a top of the column in the first side, a bottoms outlet in the bottom of the column in the first side, and an overhead outlet in the top of the column in the second side;

(b) at least one processor;

(c) at least one non-transitory computer-readable media storing computer-executable instructions; and (d) at least one receiver configured to receive data associated with at least one line in fluid communication with the column for fractionating.

8. The system of claim 7 wherein the at least one receiver is further configured to receive data from a sensor on a line in fluid communication with said column.

9. The system of claim 7 wherein the at least one receiver is further configured to record data on the composition and/or condition of a stream in said at least one line in fluid communication with said column.

10. The system of claim 7 further comprising an input/output device to provide input/output data to the at least one processor.

* * * * *